United States Patent [19]

Dierdorf et al.

[11] Patent Number: 5,693,852
[45] Date of Patent: Dec. 2, 1997

[54] PROCESS FOR THE PREPARATION OF O-ACYLOXYCARBOXANILIDES

[75] Inventors: Andreas Dierdorf; Theodor Papenfuhs, both of Frankfurt; Siegfried Planker, Königstein, all of Germany

[73] Assignee: Hoechst Aktiengesellschaft, Germany

[21] Appl. No.: 597,884

[22] Filed: Feb. 7, 1996

[30] Foreign Application Priority Data

Feb. 9, 1995 [DE] Germany ................. 195 042 25.5

[51] Int. Cl.⁶ ................................................ C07C 67/02
[52] U.S. Cl. ................................................ 560/250
[58] Field of Search ................................. 560/250

[56] References Cited

U.S. PATENT DOCUMENTS

| | | |
|---|---|---|
| 3,870,740 | 3/1975 | Fischer et al. . |
| 4,334,073 | 6/1982 | Diehr . |

FOREIGN PATENT DOCUMENTS

| | | |
|---|---|---|
| 14409 | 8/1980 | European Pat. Off. . |
| 2201432 | 7/1973 | Germany . |
| 3038598 | 5/1982 | Germany . |

OTHER PUBLICATIONS

H. Pielartzik et al. 'Houben–Weyl "Methoden der organischen Chemie," Band E5, 1985', Georg Thieme Verlag, Stuttgart, New York. pp. 684–690.

*Primary Examiner*—Samuel Barts
*Attorney, Agent, or Firm*—Connolly and Hutz

[57] ABSTRACT

The present invention relates to a process for the preparation of O-acyloxycarboxanilides of the formula (I)

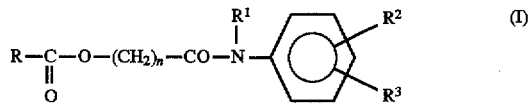

in which R is a radical having 1 to 6 carbon atoms, n is an integer from 1 to 10, $R^1$ is hydrogen or an alkyl radical having 1 to 12 carbon atoms, $R^2$ and $R^3$ are identical or different and are hydrogen, an alkyl radical having 1 to 12 carbon atoms, an aryl radical having 6 to 12 carbon atoms, a cycloalkyl radical having 5 to 12 carbon atoms in the ring, an alkenyl or alkynyl radical having 3 to 12 carbon atoms, $NO_2$, F, Cl, Br or CN, by reacting a chlorocarboxanilide of the formula (II)

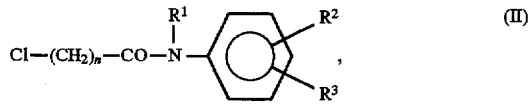

in which n, $R^1$, $R^2$ and $R^3$ have the abovementioned meaning, with an alkali metal carboxylate of the formula (III)

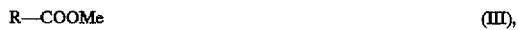

in which R has the abovementioned meaning and Me is an alkali metal, in the presence of an inert solvent and of a carboxylic acid having 1 to 6 carbon atoms, at 50° to 200° C.

16 Claims, No Drawings

PROCESS FOR THE PREPARATION OF O-ACYLOXYCARBOXANILIDES

The present invention relates to an improved process with respect to the prior art for the preparation of O-acyloxycarboxanilides.

O-Acyloxycarboxanilides, in particular acetoxyacetanilides, are interesting precursors for the preparation of glycolanilides. Glycolanilides, in turn, are used as important starting substances both in the preparation of herbicides (EP-A-300 344) and pharmaceutical active compounds (EP-A-284 338, EP-A-363 284) and in the preparation of fungicides (U.S. Pat. No. 4,440,780).

On account of the importance of this substance group, in the past there has been no lack of attempts to make hydroxycarboxamides and, in particular, hydroxycarboxanilides, for example glycolanilides, accessible by different routes. One of these routes consists in reacting an α-chlorocarboxamide with an alkali metal formate or alkali metal acetate in the presence of a quaternary ammonium salt.

German Offenlegungsschrift 30 38 598 describes a process for the preparation of α-hydroxycarboxamides by transesterification of acetoxycarboxamides by means of alcohols in the presence of catalytic amounts of an alkali metal or alkaline earth metal hydroxide or carbonate. The appropriate α-halocarboxamides are reacted with an alkali metal or alkaline earth metal acetate in the presence of a quaternary ammonium salt and if appropriate using a diluent to give the corresponding α-acetoxycarboxamides, which are then reacted.

U.S. Pat. No. 4,334,073 relates to a process for the preparation of α-hydroxycarboxamides, an α-halocarboxamide first being reacted with an alkali metal acetate or alkaline earth metal acetate in the presence of a quaternary ammonium salt and of a solvent, and the α-acetoxycarboxamide obtained then being decarboxylated to give the corresponding α-hydroxycarboxamide.

It is disadvantageous that the preparation of acetoxycarboxamides is carried out using quaternary ammonium salts. It is known, for example, that quaternary ammonium salts of this type are undesirable, in particular in the waste water, as they lead to problems in waste water purification.

A further disadvantage is that the use of a quaternary ammonium salt by no means guarantees a reaction which leads in an acceptable reaction time to a good yield (defined as conversion x selectivity). This is confirmed by the comparison experiment carried out according to U.S. Pat. No. 4,334,073.

In respect of the importance of O-acyloxycarboxanilides, in particular acetoxyacetanilides, as precursors for the preparation of glycolanilides, it is an interesting object to provide a process for the preparation of O-acyloxycarboxanilides which on the one hand avoids the disadvantages of the abovementioned processes, on the other hand can be carried out in a simple manner and using easily accessible starting substances and additionally yields the desired O-acyloxycarboxanilides both in good yield and in high purity.

This object is achieved by a process for the preparation of O-acyloxycarboxanilides of the formula (I)

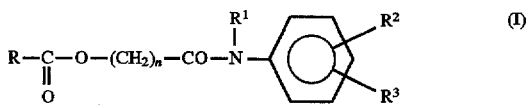

in which R is a radical having 1 to 6 carbon atoms, n is an integer from 1 to 10, $R^1$ is hydrogen or an alkyl radical having 1 to 12 carbon atoms, $R^2$ and $R^3$ are identical or different and are hydrogen, an alkyl radical having 1 to 12 carbon atoms, an aryl radical having 6 to 12 carbon atoms, a cycloalkyl radical having 5 to 12 carbon atoms in the ring, an alkenyl or alkynyl radical having 3 to 12 carbon atoms, $NO_2$, F, Cl, Br or CN. It comprises reacting a chlorocarboxanilide of the formula (II)

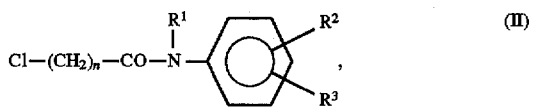

in which n, $R^1$, $R^2$ and $R^3$ have the abovementioned meaning, with an alkali metal carboxylate of the formula (III)

in which R has the abovementioned meaning and Me is an alkali metal, in the presence of an inert solvent and of a carboxylic acid having 1 to 6 carbon atoms, at 50 to 200° C.

The process according to the invention has several advantages. On the one hand, it is not restricted to the preparation of acetoxyacetanilides, but is generally suitable for the preparation of O-acyloxycarboxanilides in accordance with the reaction of the chlorocarboxanilide o of the formula (II) with the alkali metal carboxylate of the formula (III). On the other hand, the alkali metal carboxylate, the inert solvent as well as the carboxylic acid are easily accessible starting substances which can be made available even in industrial quantities. The process can be carried out in a simple manner, i.e. without a high industrial outlay, and it leads, together with higher conversions, to good yields. The desired final product is in this case obtained in very high purity.

Moreover, the use of quaternary ammonium salts can generally be dispensed with. Since the process proceeds in the absence of quaternary ammonium salts, the problems outlined above in waste water purification also do not result.

As emerges from the preceding remarks, the process according to the invention is suitable for the reaction of a relatively large number of different chlorocarboxanilides. Chlorocarboxanilides of the formula (II) in which n is an integer from 1 to 4, in particular 1 to 2, preferably 1, can thus be employed with great success.

Chlorocarboxanilides of the formula (II) are of interest in which $R^1$ is hydrogen or an alkyl radical having 1 to 4 carbon atoms and those in which $R^2$ and $R^3$ are identical or different and are hydrogen, an alkyl radical having 1 to 4 carbon atoms, $NO_2$, F, Cl, Br or CN and, in particular, $R^2$ is hydrogen and $R^3$ is an alkyl radical having 1 to 4 carbon atoms, $NO_2$ F, Cl Br or CN.

A relatively large number of different alkali metal carboxylates can be employed in the process. In particular an alkali metal carboxylates of the formula (III) can be employed in which R is hydrogen or an aliphatic radical having 1 to 5 carbon atoms, in particular an aliphatic radical having 1 to 4 carbon atoms and, independently thereof, Me is Na or K, in particular Na.

The chlorocarboxanilide and the alkali metal carboxylate can be reacted within a wide molar ratio. Customarily, the chlorocarboxanilide and the alkali metal carboxylate are used in the molar ratio 1:1 to 1:5, in particular 1:1 to 1:2.

Suitable inert solvents are aromatic or aliphatic hydrocarbons, carbons, for example toluene, o-xylene, m-xylene, p-xylene, mixtures of isomeric xylenes, ethylbenzene, mesitylene, chlorobenzene, dichlorobenzene, chlorotoluene, clyclohexane, cumene, decalin or mixtures of these solvents, in particular mixtures of isomeric xylenes and mesitylene.

It has proven suitable to use as carboxylic acid an aliphatic carboxylic acid having 1 to 6, in particular 2 to 5 carbon atoms.

Acetic acid and propionic acid have proven particularly suitable.

It is recommended to use a carboxylic acid which has the same number of carbon atoms as the alkali metal carboxylate used in each case. However, a carboxylic acid and an alkali metal carboxylate having a different number of carbon atoms can also be used; in this case products of the formula (I) are obtained in which R, on the one hand, originates from the carboxylic acid and, on the other hand, from the carboxylate.

Customarily, the alkali metal carboxylate and the carboxylic acid are used in the molar ratio 1:0.5 to 1:5, in particular 1:0.7 to 1:2. It is also possible to work below or above this molar ratio, but for this, under certain circumstances, longer reaction times or somewhat lower yields have to be accepted.

In many cases, it has proven suitable to employ inert solvent to carboxylic acid in the weight ratio 1:0.02 to 1:0.25, in particular 1:0.03 to 1:0.15, preferably 1:0.04 to 1:0.1.

For a multiplicity of reactions, it has proven adequate to allow the reaction to proceed at 70 to 170, in particular 90° to 140° C.

The alkali metal chloride formed in the reaction is separated after completion of the reaction, for example by filtration and/or extraction, for example in the form of an aqueous solution. If desired, the inert solvent can be separated by distillation and, if appropriate together with separated carboxylic acid, employed again in the reaction.

The following examples substantiate the invention, without restricting it.

EXPERIMETNAL SECTION

EXAMPLE 1

In a 250 ml flask, equipped with reflux condenser, stirrer and thermometer, 23.0 g (0.1 mol) of chloroacetic acid N-isopropyl-(4-fluoroanilide), 9.0 g (0.11 mol) of anhydrous sodium acetate, 5 ml of glacial acetic acid and 100 ml of xylene are heated to reflux temperature with stirring. The course of the reaction is monitored by means of gas-chromatographic analysis.

After completion of the reaction, the sodium chloride formed is filtered off, the solvent is removed by distillation and the residue is purified by recrystallization or distillation.

The results can be seen from Table 1 below.

TABLE 1

| Reaction time (hours) | Yield (%)* |
| --- | --- |
| 3 | 75.07% |
| 4 | 79.7% |
| 6.75 | 89.6% |

*Yield determined by gas chromatography

Comparison Example 1

(according to U.S. Pat. No. 4,334,073)

In a flask, equipped with a reflux condenser, stirrer and thermometer, 229.5 g (1 mol) of chloroacetic acid N-isopropyl-(4-fluoroanilide) in 320 ml of toluene, 82 g (1 mol) of anhydrous sodium acetate and 0.5 g of benzyltrimethylammonium chloride are heated at 115° to 120° C. for 6 hours with stirring. The course of the reaction is monitored by means of gas-chromatographic analysis.

The results can be seen from Table 2 below.

TABLE 2

| Reaction time (hours) | Yield (%)* |
| --- | --- |
| 1 | 2.9 |
| 2 | 4.5 |
| 3 | 5.7 |
| 4 | 6.8 |
| 6 | 10.3 |

*Yield determined by gas chromatography

EXAMPLE 2a and 2b

Effect of the sodium acetate to acetic acid ratio

Two batches which are identical except for the amount of acetic acid employed are used in order to investigate the effect of the sodium acetate to acetic acid ratio on the reaction time and the yield.

EXAMPLE 2a

In a flask, equipped with a reflux condenser, stirrer and thermometer, 23.0 g (0.1 mol) of N-chloroacetyl-N-isopropyl-(4-fluoroaniline) are heated to reflux temperature with stirring with 9.0 g (0.11 mol) of anhydrous sodium acetate, 6.6 g (0.11 mol) of glacial acetic acid and 100 ml of xylene. The course of the reaction is monitored by means of gas-chromatographic analysis. The results can be seen from Table 3 below.

EXAMPLE 2b

The reaction is carried out as described in Example 2a, but instead of 6.6 g of glacial acetic acid, 13.2 g (0.22 mol) of glacial acetic acid are now employed.

The results can be seen from Table 3 below.

TABLE 3

| Reaction time (hours) | Example 2a yield (%)* | Example 2b yield (%)* |
| --- | --- | --- |
| 1 | 32 | 32 |
| 2 | 54 | 54 |
| 3 | 66 | 65 |
| 4 | 75 | 75 |
| 5 | 83 | 82 |
| 6 | 87 | 83 |
| 7 | 89 | 84 |
| 8 | 91 | 86 |
| 9 | 91 | 86 |

*Yield determined by gas chromatography

EXAMPLE 3

In a flask, 57.4 g (0.25 mol) of N-chloroacetyl-N-isopropyl-(4-fluoroaniline), 20.5 g (0.25 mol) of anhydrous sodium acetate, 12.5 ml of glacial acetic acid and 80 ml of xylene are heated to reflux temperature with stirring.

The course of the reaction is monitored by means of gas-chromatographic analysis.

The results can be seen from Table 4 below.

Comparison Example 2

(without addition of glacial acetic acid)

The reaction is carried out as indicated in Example 3, but no glacial acetic acid is added.

The reaction is monitored by means of gas-chromatographic analysis.

The results can be seen from Table 4 below.

TABLE 4

| Reaction time (hours) | Comparison Example 2 Yield * | Example 3 |
|---|---|---|
| 1 | 0.5 | 33% |
| 2 | 1 | 54% |
| 3 | 1.5 | 67% |
| 4 | 2 | 76% |
| 5 | 2.5 | 82% |
| 6 | 3 | 87% |
| 7 | 3.5 | 89% |
| 8 | 4 | 91% |
| 9 | 4.5 | 92% |
| 10 | 5 | 93% |

*Yield determined by gas chromatography

EXAMPLE 4 AND COMPARISON EXAMPLE 3

Reaction of N-chloroacetyl-N-methylaniline

EXAMPLE 4

In a flask, equipped with a reflux condenser, stirrer and thermometer, 18.4 g (0.1 mol) of N-chloroacetyl-N-methylaniline, 9.0 g (0.11 mol) of sodium acetate, 6.6 g (0.11 mol) of glacial acetic acid and 100 ml of xylene are heated to reflux temperature with stirring. The course of the reaction is monitored by means of gas chromatographic analysis.

The results can be seen from Table 5 below.

Comparison Example 3

The reaction is carried out as indicated in Example 4, but no glacial acetic acid is added.

The course of the reaction is monitored by means of gas-chromatographic analysis.

The results can be seen from Table 5 below.

TABLE 5

| Reaction time (hours) | Comparison Example 3 Yield* | Example 4 Yield (%)* |
|---|---|---|
| 1 | 1 | 37 |
| 2 | 2 | 60 |
| 3 | 3 | 72 |
| 4 | 4 | 82 |
| 5 | 5 | 87 |
| 6 | 6 | 91 |
| 7 | 7 | 93 |
| 8 | 8 | 95 |
| 9 | 9 | 98 |

*Yield determined by gas chromatography

Comparison Example 4

The reaction is carried out as indicated in Example 4, but instead of 6.6 g (0.11 mol) of glacial acetic acid, 12.9 g of a 30% strength by weight aqueous HCl solution (corresponding to 0.11 mol of HCl) are added. After heating to reflux temperature for 3.5 hours, only traces of the desired valuable product (<0.2%) are detected.

EXAMPLE 5

In a flask, equipped with a reflux condenser, stirrer and thermometer, 23.0 g (0.1 mol) of N-chloroacetyl-N-isopropyl-(4-fluoroaniline), 10.6 g (0.11 mol) of sodium propionate, 8.2 g (0.11 mol) of propionic acid and 100 ml of xylene are heated to reflux temperature with stirring. The course of the reaction is monitored by means of gas-chromatographic analysis. The results can be seen from Table 6 below. In comparison with the sodium acetate/acetic acid system, a significant rise in the reaction rate is to be observed. The reaction is, for example, almost finished even after 1 hour.

Comparison Example 5

The reaction is carried out as indicated in Example 5, but no propionic acid is added. The results can be seen from Table 6 below.

TABLE 6

| Reaction time (hours) | Comparison Example 5 Yield (%)* | Example 5 Yield (%)* |
|---|---|---|
| 1 | 17 | 94 |
| 2 | 28 | 97 |
| 3 | 37 | 98 |
| 4 | 45 | 98 |
| 5 | 53 | 98 |
| 6 | 59 | 98 |
| 7 | 64 | 98 |
| 8 | 68 | 98 |
| 9 | 72 | 98 |
| 10 | 76 | 98 |

*Yield determined by gas chromatography

We claim:

1. A process for the preparation of O-acyloxycarboxanilides of the formula (I)

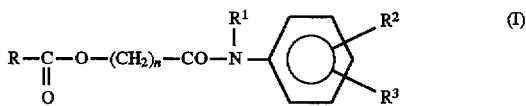

in which R is a radical having 1 to 6 carbon atoms, n is an integer from 1 to 10, $R^1$ is hydrogen or an alkyl radical having 1 to 12 carbon atoms, $R^2$ and $R^3$ are identical or different and are hydrogen, an alkyl radical having 1 to 12 carbon atoms, an aryl radical having 6 to 12 carbon atoms, a cycloalkyl radical having 5 to 12 carbon atoms in the ring, an alkenyl or alkynyl radical having 3 to 12 carbon atoms, $NO_2$, F, Cl Br or CN, which comprises reacting a chlorocarboxanilide of the formula (II)

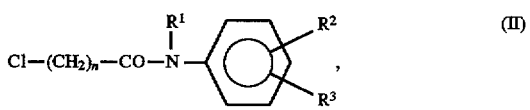

in which n, $R^1$, $R^2$ and $R^3$ have the abovementioned meaning, with an alkali metal carboxylate of the formula (III)

in which R has the abovementioned meaning and Me is an alkali metal, in the presence of an inert solvent and of a carboxylic acid having 1 to 6 carbon atoms, at 50° to 200° C.

2. The process as claimed in claim 1, wherein a chlorocarboxanilide of the formula (II) is employed in which n is an integer from 1 to 4.

3. The process as claimed in claim 1, wherein a chlorocarboxanilide is employed in which n is equal to 1.

4. The process as claimed in claim 1, wherein a chlorocarboxanilide is employed in which $R^1$ is hydrogen or an alkyl radical having 1 to 4 carbon atoms.

5. The process as claimed in claim 1, wherein a chlorocarboxanilide is employed in which $R^2$ and $R^3$ are identical or different and are hydrogen, an alkyl radical having 1 to 4 carbon atoms, $NO_2$, F, Cl Br or CN.

6. The process as claimed in claim 1, wherein a chlorocarboxanilide is employed in which $R^2$ is hydrogen and $R^3$ is an alkyl radical having 1 to 4 carbon atoms, or $NO_2$, F, Cl Br or CN.

7. The process as claimed 1, wherein an alkali metal carboxylate of the formula (III) is employed in which R is hydrogen of an aliphatic radical having 1 to 5 carbon atoms.

8. The process as claimed in claim 1, wherein an alkali metal carboxylate is employed in which Me is Na or K.

9. The process as claimed in claim 1, wherein the chlorocarboxanilide and the alkali metal carboxylate are employed in the molar ratio 1:1 to 1:5.

10. The process as claimed in claim 1, wherein toluene, o-xylene, m-xylene, p-xylene, mixtures of isomeric xylenes, ethylbenzene, mesitylene, chlorobenzene, dichlorobenzene, chlorotoluene, cyclohexane, cumene, decalin or a mixture of these solvents is/are employed as inert solvent.

11. The process as claimed in claim 1, wherein an aliphatic carboxylic acid having 1 to 6 carbon atoms is employed as carboxylic acid.

12. The process as claimed in claim 1, wherein acetic acid or propionic acid is employed as carboxylic acid.

13. The process as claimed in claim 1, wherein the alkali metal carboxylate and the carboxylic acid are employed in the molar ratio 1:0.5 to 1:5.

14. The process as claimed in claim 1, wherein inert solvent to carboxylic acid is employed in the molar ratio 1:0.02 to 1:0.25.

15. The process as claimed in claim 1, wherein the reaction is carried out at 70° to 170° C.

16. The process as claimed in claim 1, wherein the reaction is carried out at 90° to 140° C.

* * * * *